United States Patent [19]

Bloch

[11] 4,071,616

[45] Jan. 31, 1978

[54] STARCH AIR FRESHENER GELS

[75] Inventor: Daniel Richard Bloch, Racine, Wis.

[73] Assignee: S. C. Johnson & Son, Inc., Racine, Wis.

[21] Appl. No.: 768,296

[22] Filed: Feb. 14, 1977

Related U.S. Application Data

[63] Continuation of Ser. No. 634,724, Nov. 24, 1975, abandoned.

[51] Int. Cl.² .......................... A61L 9/01; A61L 9/04; B01J 13/00
[52] U.S. Cl. .................................... 424/76; 21/74 R; 106/214; 127/29; 239/54; 252/316
[58] Field of Search ................. 21/53, 74 R; 127/29; 106/210, 214; 424/76; 252/315, 316; 239/53–56

[56] References Cited

U.S. PATENT DOCUMENTS

| | | | |
|---|---|---|---|
| 2,691,615 | 10/1954 | Turner et al. | 239/54 |
| 2,824,092 | 2/1958 | Thompson | 252/316 |
| 3,265,632 | 8/1966 | Leach | 252/316 |
| 3,495,988 | 2/1970 | Balassa | 252/316 |
| 3,499,962 | 3/1970 | Wurzburg et al. | 252/316 |
| 3,655,579 | 4/1972 | Crotty et al. | 252/316 |
| 3,666,557 | 5/1972 | Jensen et al. | 252/316 |
| 3,803,045 | 4/1974 | Matsukawa et al. | 252/316 |

FOREIGN PATENT DOCUMENTS

| | | | |
|---|---|---|---|
| 6,707,457 | 12/1968 | Netherlands | 252/315 |

*Primary Examiner*—Morris O. Wolk
*Assistant Examiner*—Bradley Garris

[57] ABSTRACT

An air freshener gel comprising 2.5–15% amylose, 0.25–30% perfume, up to 5% pigment, and the balance water.

12 Claims, No Drawings

STARCH AIR FRESHENER GELS

This is a continuation of application Ser. No. 634,724, filed Nov. 24, 1975, and now abandoned.

BACKGROUND AND BRIEF DESCRIPTION OF THE INVENTION

This invention relates to air freshener gels. More particularly, this invention relates to slow diffusing solid air freshener gels formed using amylose starch as the primary gelling agent.

So-called air freshener gels have been used for a number of years to provide a relatively continuous level of perfume and/or odorant in an enclosed room. There have been a number of proposed and commercially available air freshener gels. The primary gelling agent used in most of these gels are various forms of carrageenin, a naturally occurring gelling material derived from seaweed. Although carrageenin does form a stiff gel which will dispense the perfume over an extended period of time, there are a number of disadvantages in the use of carrageenin as a primary gelling material for producing air freshener gels. The first major disadvantage is the high cost of carrageenin; second, either relatively high levels of carrageenin or additives must be used to produce a gel which has a low degree of syneresis, i.e., the appearance of free moisture on the surface of the gel; and third, carrageenin gels have a long setting time.

Although there are a number of materials which form gels, for one reason or another these materials are not particularly satisfactory for use in air freshener gel composition. However, it has been found unexpectedly that a composition utilizing from 2.5-15% amylose starch when mixed with appropriate amounts of perfume in an aqueous system produces a rigid, strong gel with substantially no signs of syneresis. These gels are inexpensive to produce and slowly release the perfume and moisture over an appropriate period of time.

OBJECTS AND ADVANTAGES

It is, therefore, the primary object of the present invention to provide a novel air freshener gel composition.

It is a further object of the present invention to provide an air freshener gel composition which is low in cost and easy to produce.

It is a still further object of the present invention to provide an air freshener gel composition based on amylose starch gels having a low degree of syneresis.

It is a still further object of the present invention to provide air freshener gels having a high strength, low syneresis, and low cost.

Still further objects and advantages of the present invention will become more apparent from the following detailed description thereof.

DETAILED DESCRIPTION AND PREFERRED EMBODIMENTS

The composition of the present invention comprises an air freshener gel consisting essentially of 2.5–15% by weight amylose starch, 0.25–30% by weight perfume, up to 5% by weight of pigment, and the balance to 100% water. Preferred compositions of the present invention comprise from 4–9% amylose starch, 0.5–2% perfume, and 0.1–1% pigment, with the balance to 100% being water. The most preferred compositions comprise from 4–7% amylose starch, 0.5–5% perfume, and 0.1–1% pigment with the balance to 100% being water.

The primary gelling agent in the air freshener gels of the present invention is amylose starch. Amylose starch, or linear starch, is a naturally occurring fraction of starch from potatoes, corn, maize, tapioca, wheat, sorghum, rice, arrow root, sago palm, and the like. Almost all naturally occurring starch compositions include some amylose and most contain from 20–30% amylose, although some high amylose corns or maize have up to 85% amylose.

The linear fraction of starch, called amylose, is a homopolymer of D-glucose. The D-glucopyranose units in amylose are substantially only linked by $(1 \rightarrow 4)$-α-glucosidic linkages as opposed to amylopectin which also has some $(1 \rightarrow 6)$-α-glucosidic linkages giving a branched structure. Amylose has the following structure:

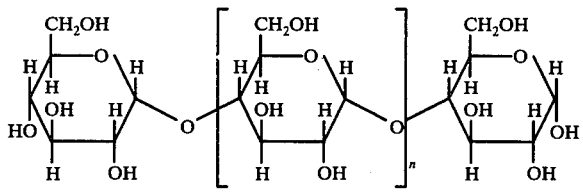

The molecular weight of amylose varies depending on the source of the amylose. The maximum number-average molecular weight for various amyloses are: Potato — 1,100,000; Tapioca — 766,000; Sago — 340,000; Wheat — 302,000; and Corn — 230,000. These weights correspond to values of $n$ of from about 200 to about 7000. Most commercially available amyloses have molecular weights of from 100,000 to 400,000. The preferred sources of amylose are potato and corn.

The gellation or retrogradation of starch and particularly amylose starch is a well-known phenomenon. Amylose will form gels in water at levels of 2.0% or greater. As added materials and impurities are included within the composition, the percentage of amylose necessary to form strong gels increases. There have been a number of uses described for amylose and starch gels. However, most of these uses are in foods and textiles. Amylose gels are said to show some syneresis. However, when used as air freshener gels, syneresis does not appear to any large extent.

Commercially available amylose starches are available having amylose content of 70% or higher, and some substantially pure, i.e., greater than 90%, amylose starches are available. These latter purified amylose starch compositions are preferred although, as will be shown in the examples, starches including 50% amylose can be used in the composition of the present invention provided the amylose content is within the range of from 2.5–12%. Often using these starches with low amylose fraction content, additional amylose is necessary to provide a rigid gel since the amylopectin acts to lower gel strength and generally from 5–12% amylose content is necessary to provide satisfactory gel when amylose mixed with up to 50% other starches is used as the gelling material.

When amylose is used having a purity of 90% or greater, satisfactory air freshener gels can be prepared at amylose content of 2.5–12% by weight. However, it is preferred to use from 4–9% amylose and most preferred to use from 4–7% amylose. The gels within the preferred range are substantially self-supporting, while gels from 2.5–4%, although satisfactory for use in tubs or other containers only open on an upper surface, are not always sufficiently rigid to be considered self-supporting.

With regard to the lower limit, at any amylose content of less than 2.5, the gels become weakened so as to become mobile gels which liquify when subjected to significant sheer forces. These gels would not be considered satisfactory as air freshener gels. Also, at an amylose content of over 12%, the processing of these air freshener gels becomes difficult because as the percentage of amylose increases the gel setting time decreases.

Perfumes which are to be included in the composition of the present invention may be any conventional water and/or oil soluble perfumes. The perfume may be present in the amounts of from 0.25–30% by weight and preferably from 0.5–5.0% and most preferred 0.5–2.0%. Most any type perfume or odorant can be used, such as citric perfumes, i.e., lemon, lime; fruits, i.e., apple, peach; floral type, i.e., rose, lilac, etc.

It has generally been thought necessary to incorporate an emulsifier to solubilize the perfume in the composition. However, if the perfume is incorporated into the gel shortly before the gel sets up, no emulsifier is necessary. However, emulsifiers can be added as optional ingredients at an amount of from 0–5% by weight. Generally nonionic emulsifiers or polysaccharide derivative emulsifiers are satisfactory. If polysaccharide emulsifiers are used, they should be added after the amylose is diluted to the final level.

An important optional component to the present compositions is a pigment which may be present in amounts up to 5% by weight and preferably from 0.1–1.0% by weight. The term "pigment" as used in this specification and the appended claims means any material useful as a coloring agent such as true pigments, dyes, lakes, etc. Although pigments are not necessary to the function of compositions of the present invention, they do add to the aesthetics of the total composition.

The water which forms the bulk of the composition can be either deionized, distilled, or ordinary tap water.

The compositions of the present invention also may include other optional ingredients, such as antimicrobial agents, antibacterial agents, and preservatives to prevent the growth of mold, etc. Small amounts of these materials which are not deleterious may be added to the composition. Occasionally, the perfumes themselves may function as mold and/or bacterial inhibitors.

It is surprising that the air freshener gels of the present invention release the perfume with a sufficient level so as to be considered satisfactory air freshener gels.

The processing of the air freshener gels of the present invention is not complicated. The amylose is heated together with the water as a relatively concentrated solution, i.e., 10–20% solids in a jet cooker. Pure amylose or amylose having a low concentration of amylopectin has a low viscosity at high temperatures and, accordingly, can be processed at relatively high concentrations. After the amylose is solubilized in the hot water, at 60–100 psig and 300°–340° F., the amylose-water composition is then mixed with sufficient cool water to bring the composition to the desired final amylose content. At this time the perfume and dye can be added, and the composition is placed in appropriate containers.

The composition of the present invention will now be illustrated by way of the following examples which are for the purpose of illustration only and are in no way to be construed as limiting.

EXAMPLE 1

An air freshener gel having the following composition was prepared by jet-cooking the amylose starch at 155° C. under pressure with about 20% of the water of the composition. The jet-cooked starch is quenched to 65°–75° C. with the balance of the water to give 5% starch. This quenched stream is cooled to 60°–65° C. and blended with perfume, pigment, and preservative and filled into air freshener packages. The composition is then cooled to room temperature.

| | |
|---|---|
| Lemon perfume | 2.5 |
| Yellow pigment, Color Index #1 | 0.025 |
| Propyl parasept | 0.01 |
| Methyl parasept | 0.10 |
| 100% amylose starch* | 5.000 |
| Water | 92.365 |
| | 100.000 |

*Potato starch from Avebe, Veendam Holland.

The above composition was tested using a gel tester commercially available from Marine Colloids, Inc., Springfield, N.J. This instrument measures the force in grams required for a plunger of a given size, driven at a constant speed to rupture a gel. The above gel was tested using a small (0.431 inch) plunger and had a gel strength of greater than 500 grams. In order to be considered self-supporting, a gel must have a gel strength of 250 grams or more while if a tub or dish type dispenser or a container having a support is to be used compositions with gel strengths as low as 75 grams can be used.

EXAMPLE 2

Example 1 is repeated, except the formulation is varied as shown in Table I.

TABLE I

| Run | Amylose Starch Level % w/w | Pigment Level/Type % w/w | Perfume Level/Type % w/w | Gel Strength g. |
|---|---|---|---|---|
| A | 3.0 | — | 0.25/Rose | 40 |
| B | 3.0 | — | 0.10/Rose | 46 |
| C | 3.0 | — | 0.05/Rose | 55 |
| D | 2.5 | — | 0.25/Rose | 28 |
| E | 2.5 | — | 0.10/Rose | 20 |
| F | 2.5 | — | 0.05/Rose | 26 |
| G | 3.0 | — | — | 260 |
| H | 3.0 | 1.0/Red | 0.75/Rose | 144 |
| I | 3.0 | 0.6/Red | 0.50/Rose | 140 |
| J | 3.0 | 0.25/Red | 0.30/Rose | 168 |
| K | 3.0 | 0.10/Red | 0.10/Rose | 84 |
| L | 3.0 | 0.05/Red | 0.05/Rose | 260 |
| M | 6.0 | — | — | 2,000 |
| N | 10.0 | — | 5.00/Lemon | 2,000 |
| O | 10.0 | — | 10.00/Lemon | 1,400 |
| P | 10.0 | — | 20.00/Lemon | 1,230 |
| Q | 10.0 | — | 30.00/Lemon | 500 |
| R | 10.0 | — | 40.00/Lemon | * |
| S | 15.0 | — | 10.00/Lemon | 2,000 |
| T | 15.0 | — | 20.00/Lemon | 1,960 |
| U | 4.0 | — | — | 550 |
| V | 4.0 | 1.00/Yellow | — | 340 |
| W | 4.0 | 2.00/Yellow | — | 290 |
| X | 4.0 | 5.00/Yellow | — | * |
| Y | 6.0 | — | — | 1,740 |
| Z | 6.0 | 3.00/Yellow | — | 1,600 |
| AA | 6.0 | 5.00/Yellow | — | 1,390 |

* - Gel too soft to measure.

The gel strengths shown in Table I were measured as described on page 8 of the specification. Although there is some variation in gel strength at low levels of amylose, i.e., 3%, many of these gels are satisfactory for use as "tub-type" slow diffusing air fresheners. All gels containing more than 4.0% amylose have sufficient gel strength to be self-supporting, except Runs R and X where excess pigment or perfume is used.

EXAMPLE 3

Samples of 100% amylose aqueous gels were prepared at varying amylose concentrations. The effect of amylose concentration on gel strength is shown in Table II.

TABLE II

| Run | Amylose % w/w | G Gel Strength g. |
|---|---|---|
| A | 1.98 | 44 |
| B | 2.99 | 285 |
| C | 3.00 | 250 |
| D | 3.39 | 400 |
| E | 3.68 | 580 |
| F | 3.92 | 650 |
| G | 4.33 | 950 |
| H | 4.73 | 1,120 |
| I | 4.87 | 1,290 |
| J | 5.36 | 1,500 |
| K | 5.60 | 1,680 |
| L | 6.04 | >2,000 |
| M | 6.21 | >2,000 |
| N | 6.33 | >2,000 |
| O | 7.09 | >2,000 |

Although these gels were prepared without perfume or pigment, the proportional relationship between gel strength and amylose concentration is shown, as is the criticality of the lower limit of 2.5%.

EXAMPLE 4

The procedure of Example 2 is repeated except that Hylon 7, a 70% amylose starch available from National Starch, is substituted for the 100% amylose starch. The compositions with gel strengths are shown in Table III. These compositions contain no pigment.

TABLE III

| Run | Starch Level % w/w | Amylose Level % w/w | Perfume Level/Type % w/w | Gel Strength (g) |
|---|---|---|---|---|
| A | 3.3 | 2.31 | — | * |
| B | 4 | 2.8 | — | 20 |
| C | 5 | 3.5 | — | 130 |
| D | 6 | 4.2 | — | 190 |
| E | 6 | 4.2 | 0.25/Rose | 48 |
| F | 6 | 4.2 | 0.10/Rose | 40 |
| G | 6 | 4.2 | 0.05/Rose | 42 |
| H | 7 | 4.9 | — | 270 |
| I | 8 | 5.6 | — | 310 |
| J | 9 | 6.3 | — | 560 |
| K | 10 | 7.0 | — | 640 |
| L | 10 | 7.0 | 0.25/Rose | 500 |
| M | 10 | 7.0 | 0.10/Rose | 670 |
| N | 10 | 7.0 | 0.10/Rose | 670 |
| O | 12 | 8.4 | — | 860 |
| P | 14 | 9.8 | — | 860 |
| Q | 15 | 10.5 | 0.50/Lemon | 780 |
| R | 15 | 10.5 | 1.00/Lemon | 830 |
| S | 15 | 10.5 | 5.00/Lemon | 32 |
| T | 15 | 10.5 | 10.00/Lemon | * |
| U | 16 | 11.2 | — | 1,050 |
| V | 20 | 14 | — | 2,000 |

* - Gel too soft to be measured.
Note: All samples prepared without pigment.

As is apparent, perfumes tend to lower gel strength. Also, the inclusion of 30% amylopectin lowers the gel strength neccessitating that higher levels of amylose be used to produce acceptable gels, especially when perfume is added as would be in the compositions of the present invention.

EXAMPLE 5

The procedure of Example 2 is repeated except the starches shown in Table IV are substituted for the 100% amylose.

TABLE IV

| Run | Starch | Starch Level % w/w | Amylose Level % w/w | Perfume Level/Type % w/w | Gel Strength (g) |
|---|---|---|---|---|---|
| A | Mira-Quick | 5 | 3 | 0.25/Rose | 18 |
| B | Mira-Quick[1] | 5 | 3 | 0.10/Rose | 20 |
| C | Mira-Quick | 5 | 3 | 0.05/Rose | 20 |
| D | Mira-Quick | 10 | 6 | 1.00/Rose | 96 |
| E | Mira-Quick | 10 | 6 | 0.5/Rose | 192 |
| F | Mira-Quick | 10 | 6 | 0.25/Rose | 400 |
| G | Mira-Quick | 10 | 6 | 0.10/Rose | 440 |
| H | Mira-Quick | 10 | 6 | 0.05/Rose | 440 |
| I | Mira-Quick | 15 | 9 | 5.0/Lemon | 100 |
| J | Mira-Quick | 15 | 9 | 2.0/Lemon | 320 |
| K | Mira-Quick | 15 | 9 | 1.0/Lemon | 280 |
| L | Mira-Quick | 15 | 9 | 0.5/Lemon | 640 |
| M | Corn Starch | 10 | 2.5 | 0.5/Lemon | * |
| N | Corn Starch[2] | 15 | 3.75 | 0.5/Lemon | * |

*Too soft to measure
[1]Mira-Quick; amylose content 55-60%; available from A.E. Staley Mfg. Co.
[2]Corn Starch; amylose content 25%; available from CPC International Corn Starch at 25% amylose is unacceptable since gels are not formed and above 15% the slurry is too thick to pump. Although Mira-Quick does not form very rigid gels as the amylose content is raised above 6%, acceptable gels are produced.

EXAMPLE 6

A series of gels are prepared using the procedure of Example 1. Each gel contains 6% pure potato amylose available from Avebe (Holland) and 1% of perfume as supplied by the perfume manufacturers. These perfumes are proprietary materials and may have various concentrations. The perfumes and gel strengths are shown below.

| Run | Perfume | Gel Strength (g) |
|---|---|---|
| A | None | >2,000 |
| B | Spice | 1,840 |
| C | Mint | 1,440 |
| D | Peach | 1,460 |
| E | Apple | 1,830 |
| F | Pine | 1,780 |
| G | Menthol (pure) | 100 |
| H | Sweet Oriental Powdery | 1,700 |
| I | Lime | 1,860 |
| J | Rose | 1,600 |
| K | Lemon | 1,600 |
| L | Floral | 2,000 |

Of these perfumes, only Menthol substantially decreased the gel strength. Since Menthol is a pure material which appears to adversely co-act with the amylose while the others are mixtures of various organic components, this result is not totally unexpected.

EXAMPLE 7

To show the effect of various emulsifiers on the compositions of the present invention, the compositions shown in Table V were prepared using the procedure of Example 1 modified by adding the emulsifier to the perfume before blending. A 5% amylose level and 2.5% lemon perfume level are used.

TABLE V

| Run | Surfactant Level 100% Solids Basis | Surfactant_A | Type_B | Gel Strength_C g. | Dispersing Ability_D |
|---|---|---|---|---|---|
| A | 2.0 | Arquad 2HT_1 | C | * | 1 |
| B | 0.5 | Arquad 2HT_1 | C | 80 | 1 |
| C | 2.0 | Hyamine 1622_2 | C | * | 1 |
| D | 0.5 | Hyamine 1622_2 | C | * | 1 |
| E | 2.0 | Triton X-100_3 | N | 140 | 1 |
| F | 0.5 | Triton X-100_3 | N | 110 | 2 |
| G | 2.0 | Emcol 511-CT_4 | N | 50 | 1 |
| H | 0.5 | Emcol 511-CT_4 | N | 320 | 1 |
| I | 2.0 | Triton X-200_5 | A | L | 2 |
| J | 0.5 | Triton X-200_5 | A | L | 2 |
| K | 2.0 | Sipex EST_6 | A | L | 3 |
| L | 0.5 | Sipex EST_6 | A | * | 1 |
| M | 2.0 | Span 80_7 | N | 136 | 1 |
| N | 0.5 | Span 80_7 | N | 210 | 1 |
| O | 2.0 | Deriphat 154_8 | AMP | * | 3 |
| P | 0.5 | Deriphat 154_8 | AMP | * | 1 |
| Q | 2.0 | Miranol JEM_9 | AMP | * | 3 |
| R | 0.5 | Miranol JEM_9 | AMP | * | 1 |
| S | — | — | — | 1080 | |

_A Surfactants
_1 Arquad 2HT - Armak Co., dihydrogenated tallow dimethyl ammonium chloride.
_2 Hyamine 1622 - Rohm & Haas, di-isobutyl phenoxy ethoxy ethyl dimethylbenzyl ammonium chloride
_3 Triton X-100 - Rohm & Haas, octylphenoxy polyethoxy ethanol. HLB = 13.5
_4 Emcol 511-CT - Whitco, modified alkanolamide.
_5 Triton X-200, Rohm & Haas, sodium alkylaryl polyether sulfonate.
_6 Sipex EST - Alcolac, sodium lauryl ether sulfate.
_7 Span 80 - ICI America, sorbitan monooleate. HLB = 4.5
_8 Deriphat 154 - General Mills, disodium N-tallow beta amino dipropionate.
_9 Miranol JEM - Miranol, sodium dicarboxylic octoate.
_B Type
C = cationic; A = anionic; N = nonionic; AMP = amphoteric
_C Gel
* = Gel too soft to be measured.
L = No gel formed.
_D
1 = acceptable, no perfume visable.
2 = questionable, some perfume on top.
3 = unacceptable, large perfume layer on top.

As is apparent, most ionic surfactants destroy gel strength. The nonionic surfactants lower gel strength but form somewhat acceptable gels. Further, the HLB level does not appreciably effect the gel strength.

EXAMPLE 8

Various polysaccharides are incorporated into a gel containing 5% pure amylose produced in accordance with the procedure of Example 1. The initial slurry feed is 10% or 20% as indicated in Table VI. Some of these materials thicken the composition requiring a 10% instead of a 20% slurry.

TABLE VI

| Run | Additive | Amount % | Slurry Feed % | Gel Strength g. |
|---|---|---|---|---|
| A | Hydroxyethoxy Guar Gum Derivative | 0.1 | 20 | 500 |
| B | Hydroxyethoxy Guar Gum Derivative | 0.5 | 10 | 100 |
| C | Carrageenan | 1.0 | 10 | 280 |
| D | Carrageenan | 0.1 | 10 | 640 |
| F | Xanthan Gum | 0.5 | 10 | * |
| F | Xanthan Gum | 0.1 | 10 | 640 |
| G | Locust Bean Gum | 1.0 | 10 | * |
| H | Locust Bean Gum | 0.1 | 20 | 620 |
| I | H-Span | 0.1 | 20 | 1,300 |
| J | H-Span | 0.05 | 20 | 280 |
| K | — | — | 10 | 740 |
| L | — | — | 10 | 740 |

Gel too soft to measure.
[1] H-Span - Hydrolyzed starch polyacrylonitrile graft copolymers Disclosed in S.N. 456,911, filed April 4, 1974, Published through OTIS #PB-231,421, Listed as available June 11, 1974, 923 O.G. 386.

These materials all decrease gel strength while increasing viscosity making processing more difficult. However, acceptable gels can be produced using most materials.

What is claimed is:

1. A slow diffusing air freshener gel composition comprising about 2.5-15% by weight amylose, about 0.25-30% by weight perfume, up to about 5% by weight pigment, and the balance water, said amylose being present in the form of amylose starch having an amylose content of at least 50% by weight amylose, said gel having a gel strength of at least 75 grams.

2. The composition of claim 1 wherein said amylose is present in the form of amylose starch having an amylose content of about 90–100% by weight amylose.

3. The composition of claim 1 wherein said amylose is selected from the group consisting of corn amylose and potato amylose.

4. The composition of claim 1 wherein said composition contains from about 4 to about 9% by weight amylose.

5. The composition of claim 1 wherein said composition contains from about 0.5 to about 5% perfume.

6. The composition of claim 1 wherein said composition contains from about 0.1 to about 1.0% pigment.

7. The composition of claim 1 wherein said gel strength is at least 250 grams.

8. A self-supporting slow diffusing air freshener gel composition comprising about 4–9% by weight amylose, said amylose being present in the form of amylose starch having an amylose content of about 70 to about 100% by weight; about 0.5–5% by weight perfume; about 0.1–1% by weight pigment with the balance being water, said gel having a gel strength of at least 250 grams.

9. The composition of claim 8 wherein said composition contains about 4–7% by weight amylose.

10. The composition of claim 8 wherein said amylose is selected from the group consisting of corn amylose and potato amylose.

11. The composition of claim 8 wherein said composition contains from about 0.5-2% perfume.

12. The composition of claim 8 wherein said amylose is present in the form of amylose starch having an amylose content of about 90–100% by weight amylose.

* * * * *